United States Patent [19]

Vaughn

[11] Patent Number: 5,242,392
[45] Date of Patent: Sep. 7, 1993

[54] INTRAVENOUS PIGGYBACK FLUSH APPARATUS

[76] Inventor: Dale T. Vaughn, 1601 Claremont Ave., Independence, Mo. 64052

[21] Appl. No.: 836,776

[22] Filed: Feb. 13, 1992

[51] Int. Cl.$^5$ .............................................. A61M 5/14
[52] U.S. Cl. ........................................ 604/80; 604/81
[58] Field of Search .................................. 604/80-85, 604/56

[56] References Cited

U.S. PATENT DOCUMENTS

| | | | |
|---|---|---|---|
| 2,758,597 | 8/1956 | Elder | 604/80 |
| 4,114,617 | 9/1978 | Turner et al. | 604/80 |
| 4,256,105 | 3/1981 | Leahey et al. | 604/81 |
| 4,623,334 | 11/1986 | Riddell | 604/85 |
| 4,705,506 | 11/1987 | Archibald | 604/81 |
| 4,846,787 | 7/1989 | Aall et al. | 604/5 |
| 4,892,524 | 1/1990 | Smith | 604/246 |
| 4,902,282 | 2/1990 | Bellotti et al. | 604/258 |
| 5,002,528 | 3/1991 | Palestrant | 604/28 |

FOREIGN PATENT DOCUMENTS

| | | | |
|---|---|---|---|
| 171962 | 6/1965 | U.S.S.R. | |
| 2059776 | 4/1981 | United Kingdom | 604/81 |

Primary Examiner—John D. Yasko
Attorney, Agent, or Firm—Kenneth W. Iles

[57] ABSTRACT

An intravenous piggyback tubing flush apparatus includes a flush chamber attached to an intravenous (IV) set on the vertical tube and located lower than an IV medication bag for following administration of medication with a flush solution of normal saline from the flush chamber, which flushes the medication from the IV tubing and from a venous access device that is inserted into the patient, thereby preventing clotting of the venous access device. The flush solution automatically follows administration of the medication. An air vent on the flush chamber and a separate air vent on the medication bag facilitate the flow of medication and flush solution through the IV tubing and the venous access device. The flush chamber is located lower than the medication bag.

1 Claim, 1 Drawing Sheet

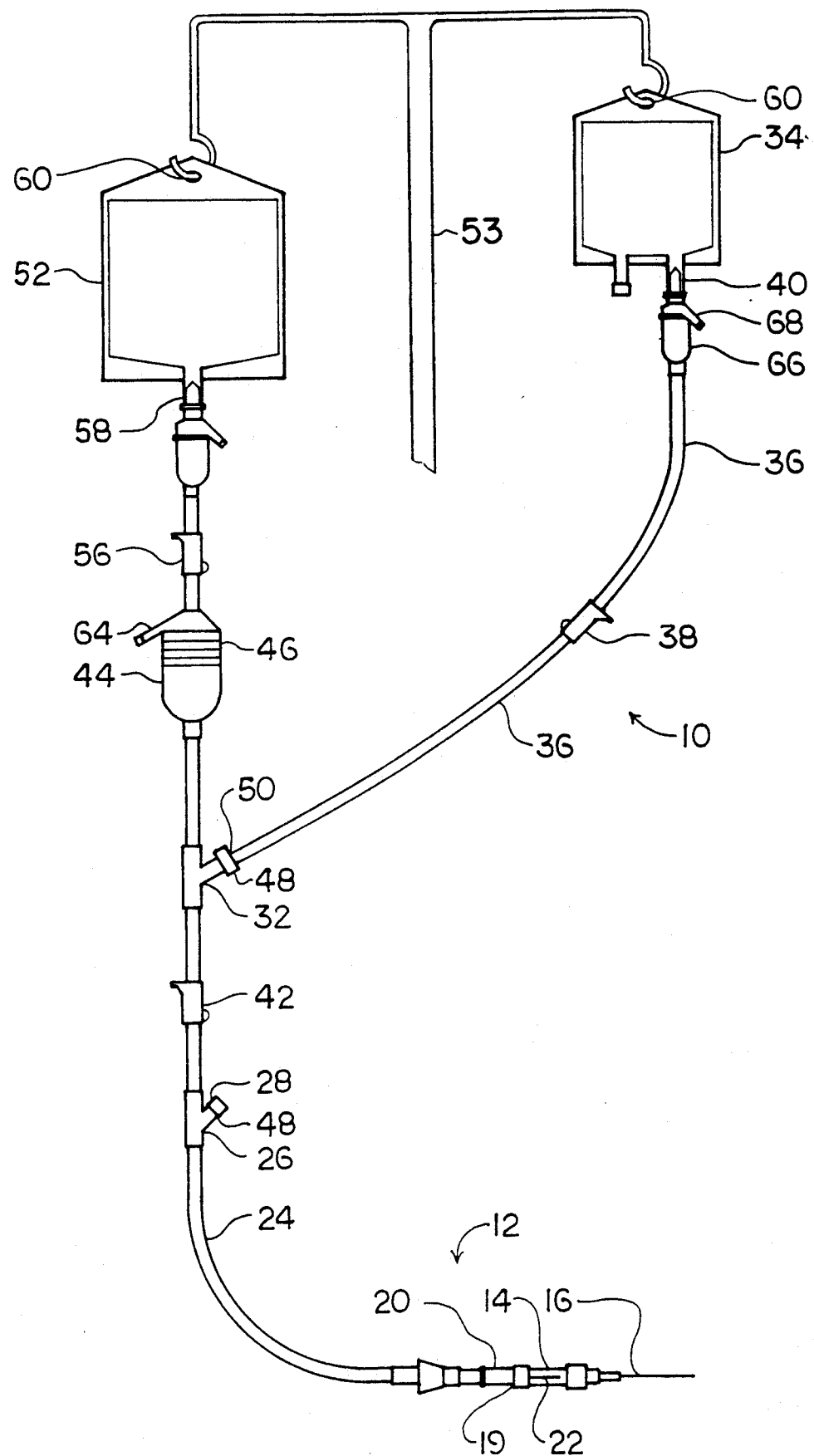

INTRAVENOUS PIGGYBACK FLUSH APPARATUS

BACKGROUND OF THE INVENTION

The present invention is related to an apparatus and process for flushing intravenous tubing (IV) after a prescribed medication has been administered through the IV. More particularly, the present invention is directed to using a flush chamber connected to the intravenous piggyback tubing system to allow the tubing to be flushed without additional needle sticks into the venous access device.

2. Description of Related Art Including Information Disclosed Under 37 C.F.R. Sections 1.97-1.99

In medical practice, it is often necessary to administer liquids to a patient intravenously. Such infusions are customarily carried out by employing intravenous kits that incorporate a supply bottle or other container of liquid that is suspended above a patient. A drop counting or drip chamber meters the dosage and gravity causes the liquid to flow through a drip tube to a venous access device (VAD), that is, a saline lock or other solution lock, which is implanted in the patient, typically in a peripheral vein in the arm.

Liquids so administered include, for example, fluids such as normal saline, blood, plasma, dextrose, glucose solutions and the like. Increasingly, however, drugs or medications, especially antibiotics are often administered through an IV device in relatively small quantities, for example, 50-150 cubic centimeters (cm) or milliliters (ml). Often such medicines are administered through intravenous tubing or IV package, but without administering any additional fluid from another bag or vessel. This procedure is followed after a patient has been fully rehydrated, if necessary, and does not need infusions of large volumes of fluid.

The infusion rate is controlled in the drip chamber by a flow controller, such as a pinch clip. When infusions are carried out, the drip tube and needle are initially purged of air, the needle is inserted into the patient, or more commonly, into the venous access device, which is separately inserted into a vein, usually in the arm. The flow controller compresses the drip tube to restrict the initial flow of liquid. The number of drops, and hence the dosage, of a liquid falling through the drip chamber are determined by trial and error adjustment of the flow controller.

Antibiotics in particular are administered intravenously because they work better when infused directly into the bloodstream than when taken orally. When administered orally, much of the dosage is destroyed in the stomach or absorbed directly by the stomach, where it is less effective than it is in the bloodstream.

Therefore, patients in need of antibiotics in a hospital are frequently given the medication intravenously for about 5-7 days, and then switched to oral medication. The antibiotics or other medications are normally administered three times each day. A period of about 30-60 minutes is required for the medications to be infused into the bloodstream by this method.

When the IV bag is empty, a health care worker removes the IV tubing from the venous access device by withdrawing the IV needle from the rubber diaphragm of the venous access device. Then the health care worker inserts a syringe needle into the diaphragm of the venous access device and flushes the venous access device with a solution to prevent clogging of the venous access device. This solution may be an anticoagulant, which is sometimes considered necessary to prevent clotting and clogging, or normal saline solution, which is frequently now used efficaciously for the same purpose.

Thus, each time a dose of medication is administered in this fashion, two needle sticks of the venous access device are required, one to insert the IV and a second to flush the venous access device after the medicine has been administered.

If a medicine in intravenously administered three times each day for five days to one patient, then 30 needle sticks of the venous access device are required during the course of IV treatment. Each of these needle sticks presents the possibility of introducing organic or infectious agents into the patient's bloodstream and the possibility of an accidental needle stick into the health care worker.

Another problem with the standard IV apparatus is that some of the medicine prescribed by the physician and typically administered by a nurse remains in the IV tubing itself, never reaching the patient. This lost medication can amount to a substantial portion of the total dosage, but physicians typically do not take this lost dosage into account when prescribing a medicine. Further aggravating this problem is the fact that IV sets provide drip tubes of widely differing inside diameters and the health care worker usually simply grasp whatever IV set is handy, so there is not any reliable way to predict exactly what proportion of the prescribed medication will remain in the IV tubing. Typically, however, it can be expected that about 3-8 cc of the medicine will remain in the tubing, which typically results in 5%-15% of the total dosage not being administered to the patient. The shortfall in medication that results sometimes depends on the patient's body weight, which is usually the basis for the prescribed dosage, and the inside diameter of the IV tubing.

As may be imagined, IV sets and the catheters they so closely resemble are useful in many health care situations and much inventive effort has been devoted to improving and refining them, as is demonstrated by the related art known to the applicant, which is discussed below.

U.S. Pat. No. 5,002,528, issued to Palestrant on Mar. 26, 1991 (Palestrant U.S. Pat. No. '528) discloses a "Percutaneous Irrigation and Drainage System" comprising an irrigation fluid reservoir located above the patient. The reservoir is connected to other elements of the invention via a three-ported connector which is also connected to a drainage bag. A body cavity of the patient is drained into the drainage bag through a small catheter. In such situations it is often necessary to irrigate the catheter several times each day to maintain the flow. This invention reduces the number of times that connections must be made and broken to accomplish the necessary irrigation. The invention does not address the problem administering medications via IV sets.

U.S. Pat. No. 4,902,282, issued to Bellotti et al. on Feb. 20, 1990 (Bellotti et al. U.S. Pat. No. '282) discloses a "Tuned Cycler Set" comprising a plurality of interconnected tubes for administering peritoneal dialysis solution in an automated peritoneal dialysis procedure. Controlling means are used to cause the flow path resistance through each flow path to be substantially equal.

U.S. Pat. No. 4,892,524 issued to Smith on Jan. 9, 1990 (Smith U.S. Pat. No. '524) discloses an "Intravenous Administration System" comprising an apparatus designed to assure a steady and unchanging overall flow rate of medicine through the system without the flow rate being affected by changes in the overall pressure of the system, such as those pressure changes caused by changes in the patient's blood pressure or physical movement. The apparatus includes a supply bottle connected to a passive meter and a regulator. The device also prevents air from flowing through it into the patient.

Aall-Flood et al. U.S. Pat. No. '787 discloses an "Apparatus for Preventing Back-Flow of fluid in a Blood Filtering System" comprising a check valve for preventing fluid back-flow between a pump and a pressure equalizer. The apparatus is employed in a blood filtering system.

Archibald U.S. Pat. No. '506 discloses a "Multiple Solution IV System with Setup Error Protection" comprising a plurality of IV sources of different solutions and a sequence valve that controls the volume of each solution that is administered to the patient and the sequence in which the solutions are administered. A pump controls and measures the accumulated volume of solution taken from each source. The care giver enters the desired volume and sequence for each solution and the invention automatically follows those instructions.

Riddell U.S. Pat. No. '334 discloses an "Intravenous Drug Infusion Apparatus" comprising a small drug mixing vessel holding a concentrated solution of medication that is connected to a VAD in the patient. A larger vessel containing a low concentration of the same medicine is physically higher than the small vessel and is connected to it by a tube that penetrates the small vessel. As solution is drained from the small vessel into the patient, it is replaced by fluid from the larger vessel, continually diluting the concentration of the medicine being administered to the patient. The invention is designed to administer a concentrated dose initially when it can be readily absorbed and utilized by the patient and to automatically decrease the dosage rate as time passes until the patient is receiving a maintenance dosage.

A Russian reference number 171962 appears to include a fluid vessel connected to a depending tube, with a portion of the tube being secured to some type of measurement device similar to a ruler or a barometer. The reference further includes a separate, lower vessel covered by a stopper which may be connected to the higher vessel, which includes an instrument along a tube from it, perhaps a thermometer. The lower vessel has a depending tube connected to it, which is in turn connected to the tubing. The reference discloses the use of two fluid reservoirs connected to a single tube with one vessel higher than the other.

None of these prior art efforts in the related field address the problems encountered in using intravenous sets for administering short antibiotics, which are summarized below.

Each time that a health care worker must attend to a patient, for example, to administer a new medication, alter a dosage, monitor a dosage, and so forth the cost of the labor involved in treating the patient increases. Clearly, having to return to a patient and remove the IV set and separately flush the venous access device increases labor costs. Further, a new syringe is used and then discarded each time the venous access device is flushed, increasing the cost of medical supplies to the patient. An apparatus and method that reduces the number of needle sticks required during the course of treatment will therefore reduce the costs of treating a particular patient.

Each time that the diaphragm of the venous access device is punctured by a needle, the risk of infection to the patient increases because it increases the possibility of introducing foreign matter into the patient's bloodstream. Conventionally, this diaphragm is punctured twice each time a dose of medication is administered, once to actually administer the medication and once to flush the venous access device.

The potential spread of Acquired Immune Deficiency Disease (AIDS) among health care workers has become a major concern. A primary source of this potential spread of AIDS is thought to be blood to blood contact caused by accidental needle sticks by health care workers to themselves. Use of intravenous systems for administering fluids and medications to patients is a major source of needle sticks to health care workers.

Therefore, a need exists for an apparatus and process that reduces the number of needle sticks required in the intravenous administration of medications, thereby reducing the possibility for accidental needle sticks into health care workers.

SUMMARY OF THE INVENTION

Accordingly, it is a primary purpose of the present invention to provide an intravenous device that reduces the number of needle sticks into the patient or the apparatus.

It is a further object of the present invention to provide an intravenous tubing flush device that can be changed only once each day, along with changing the IV set itself.

It is a further object of the present invention to provide an intravenous tubing flush device that will prevent or reduce clotting at the venous access device.

It is a further object of the present invention to provide an intravenous tubing flush device that will reduce the cost of the medical equipment required for such treatments by eliminating the need for the syringes that are conventionally used to flush the venous access device.

Conventionally, a venus access device (VAD) is inserted into a vein of a patient, secured to the patient, and left there to provide a connection for various intravenous devices. A conventional IV bag is connected to the VAD for administering medicated solutions to the patient. The tubing connecting the IV bag to the VAD remains filled with solution when the treatment is completed.

The present invention includes this conventional arrangement and further includes a second vessel or flush chamber which is connected to the conventional IV tubing at a location between the IV bag and the VAD. The flush chamber is lower than the IV bag, so that the contents of the IV bag empty before the contents of the flush chamber empty.

In another preferred embodiment, a flush fluid reservoir is suspended above the flush chamber and is connected thereto by a tube. A clamp placed between the reservoir and the flush chamber allows the health care worker to fill the flush chamber from the reservoir, eliminating the need to find normal saline to put into the flush chamber each time medication is administered. The reservoir holds enough normal saline, usually 250 cc, to insure that the flush chamber can be filled as many times as will be required during a twenty-four hour period, thereby allowing the flush chamber to be conveniently refilled throughout the one day expected life of the IV set.

In addition, the flush chamber may include an air vent to allow all the flush solution to drain through the IV set and into the patient.

In operation, the flush chamber is filled with 5, 10, or 15 cc of normal saline solution and a clamp below the bottom of the flush chamber is closed, preventing its contents from leaving the flush chamber. When it is desired to medicate the patient, the clamp to the IV bag and the clamp immediately below the flush chamber are opened. The contents of the IV bag empty into the patient via the VAD because the flush chamber is lower than the IV bag that contains the medication. When the IV bag is empty, the contents of the flush chamber, which is typically normal saline solution, empty from the flush chamber, pass through all associated tubing below the flush chamber and through the VAD.

Benefits of this use of the apparatus include flushing the tubing and the VAD to provide the patient with the entire dose of medicine prescribed by the attending physician, and cleaning out the tubing and VAD to prevent occlusion of the passages by clotting blood or other factors. This naturally reduces discomfort to the patient and reduces the likelihood of infection from repeated penetrations of the VAD. Further, the process reduces the labor involved in patient care because it is not necessary for a nurse or other care giver to revisit the patient periodically to discover when the IV bag is empty, and then separately flush the tubing and the VAD to prevent occlusion. Another benefit is that this process makes it easy to monitor the amount of normal saline used for flushing, thereby preventing administering too much normal saline.

Other objects and advantages of the present invention will become apparent from the following description taken in connection with the accompanying drawings, wherein is set forth by way of illustration and example, the preferred embodiment of the present invention and the best mode currently known to the inventor for carrying out his invention.

BRIEF DESCRIPTION OF THE DRAWING

The drawing figure is a schematic elevation of the preferred embodiment of the present invention.

DETAILED DESCRIPTION OF THE PREFERRED EMBODIMENTS

As required by the Patent Statutes and the case law, the preferred embodiment of the present invention and the best mode currently known to the inventor for carrying out the invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to employ the apparatus and process disclosed herein in any appropriately specific and detailed structure.

Referring to the drawing figure, the intravenous piggyback tubing flush apparatus 10 is advantageously includes a venous access device 12 having a coupling 14 for retaining a catheter 16 inside an arm of a patient (not shown), or other part of a patient's body. The flush apparatus 10 includes a needle coupling 20 for retaining a needle 22 that is inserted into the diaphragm 19 of the VAD 12. A primary tube 24 is connected into the needle coupling 20. A side port 26 angles off to one side of the primary tube 24 for providing access to the patient for another medication if desired, without having to puncture the patient's skin again. As shown in the drawing figure, the side port 26 is sealed with a cap 28 and is not used.

Above the side port 26 along the tube 24 is a clamp 42, which can be used to close off the flow of fluids through the tube 24 from any point above the clamp 42.

Above the clamp 42 is a second side port 32, which is connected to an IV piggyback bag 34 or other container by a tube 36 having a clamp 38 interposed between the IV piggyback bag 34 and the clamp 38. A spike fitting 40 attached to the upper, free end of the tube 36 is inserted into the IV bag 34 by puncturing it, to allow the fluid inside the IV piggyback bag 34, typically 50-150 cm of medicine in solution or suspension such as an antibiotic dissolved in an appropriate sterile solution, such as normal saline or dextrose and water solution, to flow into the patient when the clamps 38, 42 are open. The rate of flow can be adjusted by changing the pressure on the clamps. Typically, medication is administered in this fashion every six to eight hours and it take 30-60 minutes for the medication to be absorbed into the patient's bloodstream. The VAD is typically changed every 72 hours or less, with a new site in the patient's arm being used along with a new VAD.

The side ports 26, 32 conventionally include a rubber diaphragm 48 that is punctured by a needle to achieve fluid access to the tube 24. A needle 50 is used to connect the tube 36 to the port 32. Also the primary tube 24 and the IV piggyback tube 36 could be manufactured as a single unit. This construction decreases the possibility of the incidence of infection because the IV piggyback tube does not need to be punctured at the port 32.

Returning to the junction of the side port 32 with the tube 24 and continuing straight up, a clamp 42 is located between the port 32 and a flush chamber 44, which includes measuring graduations 46 for allowing easy measurement of the quantity of flush solution to be used, typically 5, 10, 15, and 20 cm of flush solution, depending on the length of the total tubing used and the internal diameter of the tubing 24. The flush chamber 44 is preferably made from a suitable plastic approved for use with medical solutions. A flush solution reservoir 5 is located above the flush chamber 44 for holding a supply of normal saline, or other suitable flush solution. The reservoir 52 is connected to the flush chamber 44 by a continuation of the tube 24 connected to a clamp 56 and spike fitting 58 when the reservoir 52 is a plastic bag or the like.

Both the IV bags 34, 52 ares suspended from a rack or stand 53 in the conventional manner by inserting a hook into an aperture 60 at the top of each IV bag 34, 52. This allows the flush apparatus 10 to be suspended at a point that is higher than the VAD 12, thereby allowing the medication and flush solution to enter the patient's bloodstream from the force of gravity.

The flush chamber 44 further includes an air vent 64, which may be opened to allow air to fill the volume vacated by the flush solution. This facilitates the flow of flush solution through the flush apparatus 10.

Below the IV bag 34 a drip chamber 66 allows for metering the flow of antibiotic solution in the IV bag 34. The drip chamber 66 further includes an air vent 68. The air vent 68 facilitates the flow of medicated liquid into the patient in a controlled manner. The air vents 64, 68 are conventional, allowing air to enter the vessels, but will not allow liquid to escape. A the drip chamber 66 further includes a spike fitting 40 for puncturing the IV bag 34.

It has been found that the flush apparatus 10 works effectively whether the flush chamber 44 is attached to the primary tube 24, that is the vertical tube, or to one of the side ports 26, 32. It has also been found, however, that better results are obtained when the flush chamber 44 of the flush apparatus 10 is located on the primary tube 24. Further, although the exact height of the flush chamber 44 relative to the IV bag 34 is not critical so long as the flush chamber 44 is below the IV bag 34, it has been found that superior results are achieved when the flush chamber 44 is only slightly below the bottom the drip chamber 66.

It has been further found that the flush apparatus 10 achieves better results when the flush chamber 44 is located lower than the IV bag 34. The fluid will drain from the IV bag 34 first, and when it is empty, the fluid in the flush chamber 44 then empties into the tube 24 and, therefore, into the patient. Thus, the entire dose of medication is administered to the patient, as the residual medication in the tube 24 is flushed into the patient, and the VAD 12 is also flushed by the flush solution, thereby preventing clotting and clogging of the VAD 12. Further, the prior measurement of the precise amount of flush solution to be used, by filling the flush chamber 44 with the desired amount of flush solution prior to administering the medication and the flush solution prevents overdosing the patient on flush solution.

In use, first, the clamps 38, 42, and 56 are closed, preventing any fluid flow through the tubes 24, 36. Then the IV bag 34 containing the prescribed medication is attached in a conventional manner to the IV set by the tube 36, along with the ancillary fittings and couplings as described above. The bag 34 typically is furnished by the pharmacy filled with the prescribed medicated solution. The flush solution reservoir 52 is filled with the desired flush solution and is attached to the flush chamber 44 by the tube 54 and associated ancillary fittings and couplings, as described above. The flush solution reservoir 52 is typically filled and sealed at the factory.

Then the clamps 56, 42, are opened, that is, the clamps along the primary tube 24, allowing the flush solution to flow into and fill the tube 24. Then both the clamps 42, 52 are closed. Next the clamp 38 is opened until the piggyback tube 36 is filled with medicated fluid. Then the needle 22 is inserted into the VAD 12.

Next, the needle 22 is inserted into the VAD 12, and the clamps 38 and 42 are both opened, allowing the medication to be administered to the patient.

When the medication has been exhausted from the IV bag 34 and has dripped into the patient, the flush solution in the flush chamber 44 automatically begins to flow through the tube 24 and into the VAD 12, and into the patient. The air vent 64 naturally allows the free flow of the flush solution into the tube 24.

When the flush chamber is empty, the flow of fluids into the patient stops. At his convenience, a health care worker returns to the patient, removes the needle 22 from the VAD 12, changes the needle and stores the apparatus 10 until it is time for the next dose of medication. This process eliminates the need for separately injecting a flush solution into the VAD 12 after the medication has all been administered and the standard IV set has been removed from the VAD 12, with the attendant benefits described above.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

I claim:

1. An intravenous piggyback tubing flush apparatus comprising:
    a. a medication bag containing a supply of liquid for suspending at a level higher than a patient, said medication bag further comprising a drip chamber on a lower portion of said medication bag and an air vent in said drip chamber;
    b. means for administering said liquid to said patient intravenously, said liquid administering means further comprising a venous access device inserted into the patient and means for connecting said venus access device to said liquid administering means, said connecting means further comprising a primary tube; and
    c. a flush chamber in fluid communication with said administering means and said primary tube, said flush chamber being lower than said medication bag, said flush chamber further comprising an air vent; and
    d. a flush solution reservoir for retaining a supply of flush solution, said flush solution reservoir being in fluid communication with said flush chamber and higher than said flush chamber and means for controllably replenishing the flush solution in said flush chamber connected to lower portion of said flush solution reservoir.

* * * * *